United States Patent [19]

Lerner et al.

[11] 4,389,395

[45] Jun. 21, 1983

[54] LOW MOLECULAR WEIGHT COMPLEX OF POLYRIBOINOSINIC-POLYRIBOCYTIDYLIC ACID AND METHOD OF INDUCING INTERFERON

[76] Inventors: A. Martin Lerner, 3570 Tuckahoe, Birmingham, Mich. 48010; Hilton B. Levy, 9400 Linden Ave., Bethesda, Md. 20814

[21] Appl. No.: 223,881

[22] Filed: Jan. 9, 1981

[51] Int. Cl.$^3$ .................. A61K 45/02; C07C 103/52
[52] U.S. Cl. .................. 424/85; 424/177; 424/180; 260/112.5 R; 536/270
[58] Field of Search ........... 424/85, 177, 180, 274; 260/112.5 R; 536/27-29

[56] References Cited

U.S. PATENT DOCUMENTS

| | | | |
|---|---|---|---|
| 3,679,654 | 7/1972 | Maes | 536/28 |
| 3,952,097 | 4/1976 | Levy | 536/22 |
| 4,018,916 | 4/1977 | Hodge | 536/28 |
| 4,024,222 | 5/1977 | Ts'o et al. | 536/24 |
| 4,124,702 | 11/1978 | Lanpson et al. | 536/28 |
| 4,130,641 | 12/1978 | Ts'o et al. | 536/28 |
| 4,224,241 | 5/1977 | Levy | 536/28 |

FOREIGN PATENT DOCUMENTS 25766 3/1981 European Pat. Off.

OTHER PUBLICATIONS

Gatmaitan, B. G., et al., Antimicrob. Ag. Chemother., vol. 17, pp. 49-54, 1980, and vol. 18, pp. 409-415, 1980.
Champney, K., et al., Injection and Immunity, vol. 25, pp. 831-837, 1979.

Primary Examiner—Blondel Hazel
Attorney, Agent, or Firm—Cullen, Sloman, Cantor, Grauer, Scott & Rutherford

[57] ABSTRACT

A nuclease resistant hydrophilic complex of polyriboinosinic-polyribocytidylic acid, poly-l-lysine and carboxymethylcellulose, wherein the nucleotide homopolymers have sedimentation coefficients of 4S and each homopolymer has a molecular weight of about 25,000 or less. When administered in a pharmacologically acceptable aqueous carrier, such as a saline solution, the complex is effective in inducing the synthesis of antiviral levels of interferon in the host, while modulating the toxicity reactions normally associated with the administration of greater molecular weight complexes of polyriboinosinic-polyribocytidylic acid, particularly hypotension.

8 Claims, No Drawings

LOW MOLECULAR WEIGHT COMPLEX OF POLYRIBOINOSINIC-POLYRIBOCYTIDYLIC ACID AND METHOD OF INDUCING INTERFERON

FIELD OF THE INVENTION

This invention relates to an interferon inducing synthetic polyribonucleotide complex having reduced toxic effects. More particularly, this invention relates to a nuclease-resistant hydrophilic complex of low molecular weight polyriboinosinic-polyribocytidylic acid useful in endogenous induction of interferon.

DESCRIPTION OF THE PRIOR ART

Interferon, a naturally occurring glycoprotein, is active in preventing or modifying viral diseases; *Interferons and Interferon Inducers*, edited by N. B. Finter, Amsterdam, North Holland Publishing, pp. 295-361 (1973). Human leukocyte interferon therapy has been successful in treating patients with chronic hepatitis B virus infection; Greenberg, et al., *Effect of Human Leukocyte Interferon on Hepatitis B Virus Infection in Patients with Chronic Active Hepatitis*, N. Engl. J. Med. 295, pp. 517-522 (1976) and herpeszoster in patients with cancer; Merigan, et al., *Human Leukocyte Interferon for the Treatment of Herpes Zoster in Patients with Cancer*, N. Engl. J. Med. 298, pp. 981-987 (1978). When used prophylactically to prevent respiratory infections due to influenza virus or rhinoviruses, intranasal exogeneous human leukocyte derived interferon decreased the symtoms and frequency of virus shedding and led to a decreased antibody production Merigan, et al., *Inhibition of Respiratory Virus Infection by Locally Applied Interferon*, Lancet No. 1, pp. 563-567 (1973).

The clinical testing and use of exogenous interferon to treat viral diseases is presently impractical because interferon is specific to the host animal, the substantial cost of processing whole blood and the problems encountered in purification of interferon. Many investigators have therefore discontinued their attempts to use interferon directly to treat diseases and have explored endogenous induction of interferon. In 1967, it was discovered that microgram quantities of polyriboinosinic-polyribocytidylic acid induced large amounts of interferon in rodents and rabbits; Field et al., *Inducers of Interferon and Host Resistance*, Proc. Natl. Acad. Sci. U.S.A. 58, pp. 1004-1010 (1967). Polyriboinosinic-polyribocytidylic acid, hereinafter referred to as "poly I:C", is a complex of synthetic double-stranded ribonucleotides, which has been found to be an effective antiviral agent, both prophylactically and therapeutically and as an antitumor agent in rodents and rabbits, Parks et al., *Herpetic Keratoconjunctivitis: Therapy with Synthetic Double-Stranded RNA*, Science 162, pp. 811-813 (1968); Worthington et al., *Late Therapy of an Arbovirus, Encephalitis in Mice with Interferon and Interferon Stimulators*, Proc. Soc. Exp. Biol. Med. 143, pp. 638-643 (1973); and Levy et al., *Inhibition of Tumor Growth in Polyinosinic-Polycytidylic Acid*, Proc. Natl. Acad. Sci. U.S.A. 62, pp. 357-361 (1970): see also U.S. Pat. No. 3,692,899 of Levy, which is incorporated herein by reference.

Unfortunately, poly I:C is rapidly hydrolized by nucleolytic enzymes in primate sera, resulting in poor interferon induction in humans; Nordlund et al., *Inhibition of Biologic Activity of Poly I: Poly C by Human Plasma*, Proc. Soc. Exp. Biol. Med. 133, pp. 439-444 (1970). More recently, a soluble complex of poly I:C with poly-l-lysine and carboxymethylcellulose [hereinafter referred to as "poly I:C-LC"] was prepared which is five to ten times more resistant to primate serum than the parent poly I:C and which induced significant levels of serum interferon in monkeys and chimpanzees under conditions in which poly I:C itself induced no interferon, Levy et al., *A Modified Polyriboinosinic-Polyribocytidylic Acid Complex that Induces Interferon in Primates*, J. Infect. Dis. 132, pp. 434-439 (1975). Poly I:C-LC was also shown to be effective in the prophylaxis of simian hemorrhagic fever, rabies, yellow fever and hepatitis in nonhuman primates; Levy, *Induction of Interferon in Vero by Polynucleotides*, Tex. Rep. Biol. Med. 35, pp. 91-99 (1977). No toxic effects due to poly I:C-LC were observed in nonhuman primates.

On the basis of these extensive tests in animal model systems, poly I:C-LC clinical trials were initiated in humans. These tests did establish that poly I:C-LC is an effective interferon inducer in man. However clinical testing was stopped in one laboratory (Wayne State University) because of the toxic effects elicited by poly I:C-LC administration. At the National Cancer Institute, for example, several toxic reactions were noted wherein 15 daily doses of 0.5 to 27.0 mg/m$^2$ were given to 19 patients with various solid tumors and to 6 patients with acute leukemia. The most consistent clinical response to intravenous injections of poly I:C-LC in cancer patients was a febrile reaction, which occurred in 100% of the trials. Additional toxic reactions included thrombocytopenia and leukopenia (68% of trials), nausea, hypotension (28%), polyarthralgia plus myalgia (16%) and erythema (12%). The appearance of hypotension and arthralgia-myalgia was found to be related to the dose level and/or magnitude of the interferon induction. Low correlation was found between the other toxic manifestations and the dosage of poly I:C-LC administered. The correlation, however, between peak serum interferon titers and dose was found to be linear. The maximum tolerated daily dose for all patients was 12 mg/m$^2$; Levine et al., *Initial Clinical Trials in Cancer Patients of Polyriboinosinic-Polyribocytidylic Acid Stabilized with Poly-l-lysine in Carboxymethylcellulose*, Cancer Res. 39, pp. 1645-1650 (1979).

In a simultaneous Phase 1 clinical trial at Wayne State University in collaboration with NIAID, 14 patients with severe viral infections were given 5 consecutive intravenous infusions of poly I:C-LC at daily doses of 0.15 to 0.30 mg/kg. Interferon was detected in the serum 8 to 16 hours after the injections. Interferon titers persisted in blood for 12 to 48 hours with the lowest level of serum interferon occurring on days 2 through 5. Fever (93% of patients) peaked 3 to 8 hours after completion of infusions, while interferon was present 8 to 16 hours after injection. Other toxic effects were lymphopenia (in 71% of patients) and hypotension (50%). The apparent increased incidents and severity of hypotension in the patients with severe viral infection compared to patients with cancer were noted. The hypotensive effects of poly I:C-LC necessitated the cessation of clinical trial of poly I:C-LC in patients with viral infections, Champney, et al., *Modified Polyriboinosinic, Polyribocytidylic Acid Complex: Sustained Interferonemia and its Physiologic Associates in Humans*, Infect. Immun. 25, pp. 831-837 (1979).

Reference is also made to U.S. Pat. Nos. 3,952,097 and 4,024,241, which are incorporated herein by reference. These patents describe in more detail the methods of preparation and administration of high molecular weight poly I:C-LC in humans and nonhuman primates. The poly I:C-LC RNA complex and method described in these patents was successful as an interferon inducer in primates, however the toxic reactions in humans, particularly hypotension, has limited its used. It is a principal object of the present invention to provide an interferon inducer which moderates or preferably eliminates the toxic effects described hereinabove, particularly hypotension.

SUMMARY OF THE INVENTION

The low molecular weight poly I:C complex of this invention is particularly adapted to modulate the hypotensive and febrile responses found in the clinical trials described above, while maintaining the interferon inducing capacity of the complex. As set forth in the above referenced United States Patents, it was believed that a high molecular weight (ie. 100,000) poly I:C complex was necessary to induce endogenous interferon in the host.

It has now been discovered that both hyperpyrexia and hypotension are due to the length of the poly I:C polymer. In the Examples described herein, poly I:C complexes with sedimentation coefficients of 9S and 6S (molecular weights of 100,000 and 50,000, respectively) induce hypotension in every subject. When a poly I:C complex having a sedimentation coefficient of 4S (molecular weight 25,000) was administered, no subject experienced falls in blood pressure. It has also been determined that the molecular weight of the nuclease stabilizing additives, namely poly-l-lysine and carboxymethycellulose, does not have any affect upon the toxic responses observed.

The preferred interferon inducing complex of this invention is a nuclease resistant hydrophilic synthetic complex of polyriboinosinicpolyribocytidylic acid with homopolymer sedimentation coefficients of 4S. Each nucleotide homopolymer has a molecular weight of 25,000. The complex also includes a stabilizing means to prevent hydrolysis of the complex in primate serum. The preferred complex includes poly-l-lysine and carboxymethylcellulose. The method of this invention thus includes preparing a pharmaceutically acceptable hydrophilic complex of a low molecular weight poly I:C having a homopolymer sedimentation coefficient of 4S and a molecular weight of 25,000 and administering the complex to a host to induce endogenous interferon in the host.

Other advantages and meritorious features of the interferon inducing complex and method of this invention will be more fully understood from the following detailed description and the appended claims. It will be understood by those skilled in the art that various modifications can be made to the ribonucleotide complex and method of this invention as described more fully hereinbelow.

DETAILED DESCRIPTION OF THE PREFERRED COMPLEX AND METHOD

The febrile, hypotensive responses in humans to poly I:C-LC (9S) described hereinabove resembles endotoxin-like effects to which humans and rabbits show a unique susceptibility; Beeson et al., *Tolerance to Bacterial Pyrogens: Factors Influencing its Development*, J. Exp. Med. 86, pp. 29-38 (1947). All of the clinical tests described hereinabove utilized high molecular weight (ie. 100,000) nucleotide polymers with sedimentation coefficients of 9S, which is hereinafter referred to as poly I:C-LC (9S). Similarly, poly I:C-LC (6S) and poly I:C-LC (4S) refer to shorter, lower molecular weight nucleotide homopolymers with sedimentation coefficients of 6S and 4S, respectively, having molecular weights of 50,000 and 25,000, respectively.

Based upon the similarity in the toxic reactions between humans and rabbits, rabbits were selected as a possible animal model for toxicity of poly I:C-LC (9S). Intravenous infusions of poly I:C-LC (9S) induced significant titers of serum interferon, fever and neutrophilic leukocytes. Hypotensions and deaths also occurred in several of the subjects. Thus, a readily available model of poly I:C-LC toxicity was found; Gatmaitan, et al., *Studies of a Modified Polyriboinosinic-Polyribocytidylic Acid Complex: Induction of Serum Interferon, Fever and Hypotension in Rabbits*, Antimicrob. Ag. Chemother. 17, pp. 49-54 (1980).

In the experiments described hereinbelow, young male New Zealand white rabbits were utilized (2.5 to 3.5 kg) purchased from Oakhill Co., Ostego, Mich. The poly I:C (9S), (6S) and (4S) complexes were prepared by P. L. Laboratories, Milwaukee, Wis. in accordance with the procedures described in Levy et al., *A Modified Polyriboinosinic-Polyribocytidylic Acid Complex that Induces Innterferon in Primates*, J. Infect. Dis. 132, pp. 434-439 (1975) and the above referenced United States Patents. Poly-l-lysine with molecular weights of 27,000, 13,800 and 3,400 were obtained from Miles Laboratories, Elkhart, Ind. Carboxymethycellulose preparations, standard viscosity (molecular weight 700,000), medium viscosity (molecular weight 250,000) and low viscosity (molecular weight 85,000) were obtained from Hercules Powder Co., Wilmington, Del. Polyriboinosinic-polyribocytidylic acid was complexed with poly-l-lysine and carboxymethylcellulose as described in the above referenced 1975 publication of Levy et al. in Volume 132, Journal of Infectious Diseases.

The concentration of poly I:C was 2 mg/ml. The concentration of poly-l-lysine was 1.5 mg/ml in 0.5% carboxymethylcellulose. The vehicle was pyrogen-free saline for injection.

Before use, the poly I:C-LC was diluted in sterile pyrogen-free normal saline. A dosage (0.2 mg/kg) of poly I:C-LC was used. This dosage of poly I:C-LC (9S) was found to be a potent interferon inducer in humans, see the 1979 publication of Champney et al., Infect. Immun., supra. The poly I:C-LC was given to rabbits either by intravenous injection, by ear vein, intramuscularly or subcutaneously. In each case, the complex was given once daily for five days. In certain experiments, hydrocortisone sodium succinate (6 mg/kg per day, hydrocortisone) was given intravenously daily over a 30 second interval, either 30 minutes before or 30 minutes after application of the poly I:C-LC. Control rabbits were given the same volume of sterile pyrogen free saline.

Rectal temperatures in rabbits were taken with an IVAC thermometer purchased from IVAC Corp., San Diego, Calif. Systolic blood pressures were measured by using the rabbit right hind limbs and a cuff (1.5 by 14 in.) attached to a transducer which magnified the Korot-koff sounds. Transducer readings correlated well with those obtained by palpation. Temperature and systolic blood pressures were recorded immediately before intravenous infusions and thereafter at 4, 8 and 24 hours daily for five days.

Two milliliters of heparinized blood were taken from the rabbit's ear for complete blood counts on each study day 4 hours after infusion of the poly I:C-LC complexes. Before infusions on days 1, 3 and 5, 8 ml of heparinized blood was taken for determination of the SMA-17 (Sequential Multiple Analysis; 17 biochemical analysis upon a single specimen of serum were performed). The SMA determination includes measures of total protein (grams per 100 ml), albumin (mg per 100 ml) glucose (mg per 100 ml) uric acid (mg per 100 ml), etc. as described in the above referenced 1980 publication of Gatmaitan, et al. in Antimicrobial Agents and Chemotherapy. Assays for serum interferon used vesicularstomatitis virus. Virus was passaged in a continuous line of rabbit kidney tissue cultures (RK-13) maintained at Hutzel Hospital, Detroit, Mich. The method of assay is described in the above referenced publication of Gatmaitan et al.

EXAMPLE I

The purposes of the experiments in this Example are to (1) compare the febrile and hypotensive responses of rabbits to poly I:C-LC (9S) with the responses previously observed in humans, (2) compare the interferon inducing capacity of poly I:C-LC (9S) by alternative routes, ie. intravenously, intramuscularly, etc., and (3) compare the febrile, hypotensive and interferon responses to poly I:C-LC (9S) with the responses to the lower molecular weight poly I:C-LC (4S) complex. The materials utilized in these Examples, including the polyribonucleotide complexes, were prepared as described above and in the above referenced patents and publications, which are incorporated herein by reference.

EXPERIMENT 1

This experiment was essentially a control study to determine the variations in body temperature, blood pressure and levels of circulating interferon in normal rabbits and the responses of the subjects to intravenous injections of poly I:C-LC (9S) and hydrocortisone. The rabbits in this experiment were divided into three groups, as follows: Group I, which consisted of four subjects, was given normal saline solution intravenously; Group II, which consisted of three subjects, was given hydrocortisone sodium succinate (hereinafter "hydrocortisone"); and, Group III, which consisted of six subjects, received poly I:C-LC (9S) intravenously. Normal systolic blood pressures ranged from 70 to 82 mm. Values <2 standard deviations from the mean were considered hypotensive. The normal rectal temperature was 101° to 102.9° F. Values >2 standard deviations from the mean were considered elevated.

Hematological and SMA-17 measurements were made on three of the six animals in Group III. Group I rabbits remained afebrile and normotensive. Sera taken at 0, 4, 8, 12 or 24 hours after the saline infusions in Group I had no detectable levels of circulating interferon. The rabbits given hydrocortisone in Group II also remained afebrile, normotensive and without circulating interferon. Among the Group III subjects, fevers peaked (103° to 105.5° F.) 4 hours after infusions of poly I:C-LS (9S) and were still abnormal (103° to 104° F.) 8 hours later. The temperatures usually returned to normal at 24 hours after infusion. At the 4th hour following infusion on days 1 and 2, severe hypotension was observed (mean systolic blood pressure <40 mm). One rabbit in Group III on day 1 had unobtainable systolic Korot-koff sounds (less than 20 mm) at 4 hours and 8 hours following infusion and was dead in the morning following the 1st infusion. Another Group III subject died 8 hours after the 2nd infusion of poly I:C-LC (9S). At the 24th hour following the 2nd to 5th infusions, the blood pressures of the rabbits in Group III had returned to normal. Beginning with infusions of the poly I:C-LC (9S) complex on day 4, the rabbits in Group III had fever and less severe hypotensive responses. No animals died after day 2.

The circulating serum interferon in the rabbits in Group III was highest 4 hours after the intravenous infusions of the poly I:C-LC (9S) complex and remained high at 8 hours following infusion. The circulating interferon level was lowest after 24 hours. Peaks in individual rabbits at 4 hours ranged from 2,500 to 10,240 U/ml. The latter rabbit with the highest interferon titer died within 24 hours after receiving the poly I:C-LC (9S) complex. Values of serum interferon decreased by day 3 and continued to decline thereafter. One rabbit produced comparatively little interferon throughout (peak 600 U/ml on day 1).

EXPERIMENT 2

The rabbits in this experiment were divided into five groups, as follows: Group I, which consisted of three subjects, received sterile saline solution intravenously; Group II, which consisted of three subjects, received the poly I:C-LC (9S) complex intravenously, followed by an intravenous injection of hydrocortisone 30 minutes later; Group III, which consisted of three subjects, was given hydrocortisone intravenously, followed by intravenous injections of poly I:C-LC (9S) 30 minutes later; Group IV, which consisted of four subjects, was given poly I:C-LC (9S) intramuscularly; and, Group V, which consisted of four subjects, was given poly I:C-LC (9S) subcutaneously. No rabbits died in this experiment.

As expected, the rabbits in Group I which received sterile saline solution were afebrile and and normotensive, without circulating serum interferon. The rabbits in Group II which received the poly I:C-LC (9S) complex followed by hydrocortisone showed a modest lowering of their systolic blood pressures (falls about equal to 15 mm) and their rectal temperatures did not exceed 104.5° F. At 4 hours after the intravenous injection, mean peak interferon titers of 1,800 U/ml and 750 U/ml were seen on experimental days 1 and 2, respectively. When the hydrocortisone injection preceded the poly I:C-LC (9S) in Group III, blood pressures and temperatures remained normal, but mean interferon titers on day 1 (410 U/ml) and 2 (200 U/ml) were significantly muted. It was determined that poly I:C-LC (9S) given either intramuscularly or subcutaneously in Groups IV and V did not induce falls in systolic blood pressure, but fevers were similar to those obtained after intravenous dosing. Peak interferon titers were minimal, only several hundred units per milliliter.

EXPERIMENT 3

The purpose of this experiment was to determine whether administration of a preparation of a lower molecular weight polyribonucleotide complex, poly I:C-LC (4S), might retain the capacity to induce high titers of serum interferon, while reducing or avoiding the untoward toxic responses. The rabbits in this experiment were divided into four groups of four subjects each, as follows: Group I received the poly I:C-LC (4S) complex intravenously; Group II received the poly I:C-LC (4S) complex intramuscularly; Group III received the poly I:C-LC (9S) complex intravenously; and, Group IV received the poly I:C-LC (9S) complex intramuscularly.

The lower weight poly I:C-LC (4S) complex given intravenously in Group I produced significant mean peak interferon titers on day 1 (1,500 U/ml), day 2 (1,000 U/ml) and day 3 (400 U/ml) of this series without inducing hypotension. The poly I:C-LC (4S) injected intramuscularly in Group II induced much lower titers of interferon (mean peak 150 U/ml), confirming earlier findings that higher titers of interferon are induced in rabbits by intravenous injection using poly I:C (9S). Pyrexia occurred in all groups, including the subjects injected with poly I:C-LC (4S), intravenously and intramuscularly, Groups I and II. Groups III and IV behaved as described above in experiment 2. That is, Group III, which received poly I:C-LC (9S) intravenously had high titers of interferon, febrile and hypotensive responses. Group IV, which received poly I:C-LC (9S) intramuscularly, did not have significant falls in systolic blood pressure, but peak interferon titers were only several hundred units per milliliter.

Throughout experiments 1 to 3 above, all values of the SMA-17 remained normal. Normal absolute neutrophile counts were 2,500 to 5,000 cells/mm$^3$. Poly I:C-LC (9S), poly I:C-LC (4S) and hydrocortisone-induced absolute neutrophilic leukocytes (5,100 to 10,000 cells/mm$^3$) which persisted throughout.

The results of the three experiments above are summarized qualitatively, as follows:

| Procedure | Serum Interferon | Fever | Hypotension |
|---|---|---|---|
| Normal saline, i.v. | None | None | None |
| Hydrocortisone (HC), i.v. | None | None | None |
| poly I:C-LC (9S), i.v. | Marked | Marked | Marked |
| poly I:C-LC (9S), followed by HC, i.v. | Moderate | Moderate | Moderate |
| HC, followed by poly I:C-LC (9S), i.v. | Minimal | None | None |
| poly I:C-LC (9S), i.m. | Minimal | Marked | None |
| poly I:C-LC (9S), s.c. | Minimal | Marked | None |
| poly I:C-LC (4S), i.v. | Marked to moderate | Marked | None |
| poly I:C-LC (4S), i.m. | Minimal | Marked | None |

The experiments on rabbits of this Example with poly I:C-LC (9S) indicates that, as in humans, intravenous infusions of the synthetic polyribonucleotide complex induces significant titers of serum interferon, fever and neutrophilic leukocytosis. The severe hypotension response observed in humans which required cessation of clinical testing in one laboratory also occurred in the rabbits tested. The hypotensive response was not observed in the animal studies in mice, monkeys or chimpanzees referred to in the publications cited hereinabove.

In rabbits, serum interferon and hypotension was maximum on days 1 and 2 and diminished on days 3 to 5 with daily infusions of either the higher molecular weight polyribonucleotide, poly I:C-LC (9S), and the lower molecular weight nucleotide, poly I:C-LC (4S). A hyporesponsive state, therefore, develops in rabbits to poly I:C-LC, as it does in humans. Hypotension induced by the greater molecular weight poly I:C-LC (9S) and the level of the titers of interferon in serum were less when poly I:C-LC (9S) was given intramuscularly or subcutaneously. In this respect, rabbits are also distinct from monkeys or chimpanzees, for in these animals intramuscular injections produced high interferon titers; see Sammons, *Interferon Induction in Cynomolgus and Rhesus Monkeys After Repeated Doses of a Modified Polyriboinosinic-Polyribocytidylic Acid Complex*, Antimicrob. Ag. Chemother, 11, pp. 80-83 (1977). It is also noteworthy that in primates peak interferon titers appeared about 8 hours after being given poly I:C-LC (9S), but regularly occurred at 4 hours in rabbits. Hydrocortisone, given either before or after the injection of poly I:C-LC (9S), ameliorated, but did not completely abolish, adverse toxic effects in rabbits, particularly the lowering of the systolic blood pressure. No rabbits, however, died when they were given hydrocortisone with intravenous poly I:C-LC (9S).

The hypotensive effects in rabbits infused with poly I:C-LC (9S) resembles similar findings in these species with endotoxin. Tolerance to both pyrexic and hypotensive effects of Salmonella typhosa, for instance, is related to rapid removal of this endotoxin from blood, presumably by facilitating mononuclear phagocytic cells within the liver, spline and lungs, see Beeson, *Tolerance to Bacterial Pyrogens: Factors Influencing its Development*, J. Exp. Med. 86, pp. 39-44 (1947). When poly I:C-LC (9S) is given intravenously to primates, it was found that the ribonucleotide macropolymer is removed from the circulation within 4 hours. The smaller molecule, interferon having a molecular weight of 17,500 is excreted over a period of hours, probably mainly by the kidneys.

Poly I:C-LC (9S) and poly I:C-LC (4S) injected intramuscularly or subcutaneously does not induce high titers of serum interferon in rabbits. More importantly, poly I:C-LC (4S) injected intravenously induces significant serum interferon titers without causing hypotension.

EXAMPLE II

The purposes of the experiments of this Example are to determine (1) the effect of the length or molecular weight of the polyribonucleotide complexes upon febrile, hypotensive and interferon response using poly I:C-LC (4S), (6S) and (9S), and (2) the effect of variations in the molecular weight of the poly-l-lysine and carboxymethycellulose in the complex. In this Example, the rabbit subjects were divided into twelve groups, with three subjects in each group. The molecular weight of the poly-l-lysine in the complex was as follows: $L_1$ was 27,000, the same as in the prior Example; $L_2$ was 13,800; and, $L_3$ was 3,400. The molecular weight of the carboxymethycellulose was as follows: $C_1$ was 700,000, the same as in the prior Example; $C_2$ was 250,000; and, $C_3$ was 85,000. The groups and the responses are summarized as follows:

| Group | Polynucleotide Complex | Serum Interferon | Fever | Hypotension | Death |
|---|---|---|---|---|---|
| I | Normal Saline | 0 | 0 | 0 | 0 |
| II | poly I:C-$L_1C_1$ (9S) | + | + | + | + |
| III | poly I:C-$L_1C_1$ (9S)* | + | + | + | + |
| IV | poly I:C-$L_1C_1$ (9S)+ | + | 0 | + | 0 |
| V | poly I:C-$L_2C_1$ (9S) | + | + | + | 0 |
| VI | poly I:C-$L_3C_1$ (9S) | + | + | + | + |
| VII | poly I:C-$L_1C_2$ (9S) | + | + | + | + |
| VIII | poly I:C-$L_1C_3$ (9S) | + | + | + | 0 |
| IX | poly I:C-$L_1$ (9S) | + | + | + | + |
| X | poly I:C-$L_1C_1$ (6S) | + | + | + | + |
| XI | poly I:C-$L_1C_1$ (4S) | + | + | 0 | 0 |
| XII | poly I:C-$L_1C_1$ (4S)+ | + | 0 | 0 | 0 |

*Addition of diphenhydramine
+Addition of indomethacin

Except for the subjects in Group I which received normal saline, each rabbit which received a polyribonucleotide complex by intravenous injection developed high titers of serum interferon. Mean peak titers of serum interferon in each group were highest (1,500–3,000 U/ml) 4 hours after infusions and remained at about two-thirds of the summits at 8 hours. After 24 hours, only 150 to 300 U/ml remained. On days 2 through 5 of each series, serum interferon titers were progressively lower, such that by the 4th and 5th infusion, peak titers at 4 hours were only 100 to 300 U/ml.

These results confirm the responses found in the prior Example, namely, that the modified complexes of each preparation of poly I:C-LC with polymer sizes of 6S and 4S, as well as the original 9S, induced high titers of serum interferon in rabbits. The use of the lower molecular weight carboxymethylcellulose ($C_2$ or $C_3$) or poly-l-lysine ($C_2$ or $C_3$) or even the absence of carboxymethylcellulose in Group IX did not alter the resultant serum interferon titer.

With the exception of the subjects in Group IV, which received poly I:C-LC (9S), and Group XII, which received poly I:C-LC (4S) with simultaneous intravenous injections of indomethacin, each rabbit in every group which received the modified double-stranded polyribonucleotides became hyperpyrexic. Throughout each of the 5 days of these experiments, the subjects remained febrile, except, of course, Group I. Mean temperature curves for each group peaked at 4 hours after infusion of the polyribonucleotide complexes and were generally lowest 24 hours later. Fevers were slightly less on the 4th and 5th days of each series, but ameliorations of pyrexia were not as pronounced as were the decrements in peak serum interferon titers. Simultaneous administration of indomethacin completely prevented the febrile responses in Group IV which received poly I:C-LC (9S), without altering the serum interferon titers.

Significant falls in systolic blood pressures occurred in every subject of all groups with the exception of Groups XI and XII, which received poly I:C-LC (4S). Otherwise, mean blood pressures were depressed by 10 mm or more 4 hours after intravenous infusions. The mean blood pressures were still low at 8 hours and sometimes had not recovered by 24 hours. In general, however, the hypotensive responses were somewhat lessened on the 3rd through the 5th days. Nevertheless, subjects died in shock on each experimental day. For example, in Group II, which received poly I:C-$L_1C_1$ (9S), one subject died on day 2. In Group III, which received poly I:C-$L_1C_1$ (9S) with a simultaneous injection of diphenhydramine, one subject died on day 2. In Group VI, which received poly I:C-$L_2C_1$ (9S), one subject died on day 2 and a second died on day 5. In Group VII, which received poly I:C-$L_1C_2$ (9S), one subject died on day 1 and another died on day 2. In Group IX, which received poly I:C-$L_1$ (9S), one subject died on day 2. In Group X, which received poly I:C-$L_1C_1$ (6S), one subject died on day 2 and another died on day 4.

Therefore, except for the polymer complexes containing poly I:C (4S), both the 9S and 6S polyribonucleotides, along with the several modifications of the molecular weight of poly-l-lysine and carboxymethylcellulose, did not alter the capacity of the complex to dangerously lower the blood pressure of the subjects.

All values of the SMA-17 remained normal. Absolute neutrophil counts among the subjects in the saline control group, Group I, were 2,500 to 5,000 cells/mm$^2$. Every polyribonucleotide complex used, comprising Groups II to XII, induced neutrophilic leukocytoses of 10,000 to 15,000 cells/mm$^2$, which persisted for 5 days. Administrations of diphenhydramine and indomethacin did not affect elevations in white blood cell counts.

SUMMARY

These experiments demonstrate that both hyperpyrexia and hypotension in rabbits are wholly due to the length of the poly I:C polymer. Poly I:C complexes with sedimentation coefficients of 9S and 6S at doses of 0.2 mg/kg per day induced hypotension in every subject and caused shock and death in each group. When poly I:C (4S) was used, no animal experienced significant falls in blood pressure and none died. Neither the molecular weight of the poly-l-lysine (27,000, 13,800 or 3,400), nor the molecular weight of carboxymethycellulose (700,000, 250,000 or 85,000) of the modified complexes affected the toxic response observed. The function of the poly-l-lysine and the carboxymethycellulose appeared only to stabilize the internucleotide complexes of the polyriboinosinic-polyribocytidylic acid polymer to phosdiesterases of primate serum which, of course, are not present in rabbit serum.

The responses of rabbits were found to be very similar to the responses previously observed in humans in the clinical tests described in the publications referenced hereinabove. The toxic responses were not observed in rodent or nonhuman primates. Therefore, it is reasonable to assume that poly I:C-LC will raise significant titers of interferon in humans, while ameliorating the hypotensive and febrile toxic responses. In fact, no hypotensive response was found in rabbits using the modified poly I:C-LC (4S) complex. Further, simultaneous application of indomethacin eliminated the febrile response using the poly I:C-LC (4S) complex.

The nuclease resistant hydrophilic complex of this invention of polyriboinosinic-polyribocytidylic acid, poly-l-lysine and carboxymethycellulose, wherein the nucleotide polymers have sedimentation coefficients of 4S and molecular weights of 25,000 is therefore an important breakthrough in the synthesis of endogenous interferon. The method of this invention, which comprises inducing the synthesis of endogenous interferon in a host, consists of administering the nuclease resistant hydrophilic complex of polyriboinosinic-polyribocytidylic acid having homopolymer sedimentation coefficients of 4S and a molecular weight of 25,000, complexed with poly-l-lysine and carboxymethycellulose. As described in the above referenced publications, the method of this invention may be used as an antiviral agent, both prophylactically and therapeutically, and as an antitumor agent.

I claim:

1. A nuclease resistant hydrophilic complex of the nucleotide homopolymers polyriboinosinic and polyribocytidylic acid having homopolymer sedimentations coefficients of 4S, each homopolymer having a molecular weight of 25,000 or less, said complex including a stabilizing means adapted to stabilize the internucleotide linkages of the polyriboinosinic, polyribocytidylic acid polymer to phosdiesterases of primate serum.

2. The nuclease resistant hydrophilic complex of claim 1, wherein the stabilizing means is poly-l-lysine and carboxymethylcellulose.

3. A nuclease resistant hydrophilic complex of polyriboinosinicpolyribocytidylic acid, poly-l-lysine and carboxymethycellulose, wherein the nucleotide homopolymers have sedimentation coefficients of 4S and each polymer has a molecular weight of about 25,000 or less.

4. An injectable preparation in a pharmaceutically acceptable aqueous carrier of a nuclease-resistant hydrophilic complex of a relatively low molecular weight polyriboinosinic-polyribcytidylic acid, poly-l-lysine and carboxymethycellulose, wherein the nucleotide homopolymers have sedimentation coefficients of 4S and each homopolymer has a molecular weight of about 25,000 or less.

5. A method of inducing the synthesis of interferon in a host which comprises administering a nuclease resistant hydrophilic complex of homopolymers of polyriboinosinic and polyribocytidylic acid having homopolymer sedimentation coefficients of 4S, each homopolymer having a molecular weight of about 25,000 or less and said complex including a stabilizing means adapted to stabilize the internucleotide linkages of the polyriboinosinic-polyribcytidylic acid polymer to phosdiesterases of primate serum.

6. The method of including the synthesis of interferon defined in claim 5, characterized in that said stabilizing means is poly-l-lysine and carboxymethycellulose.

7. The method of inducing the synthesis of interferon defined in claim 5, including the concomitant administration of an antipyretic agent.

8. The method of inducing the synthesis of interferon defined in claim 7, characterized in that said antipyretic agent is indomethacin.

* * * * *